United States Patent [19]

Paxson et al.

[11] 4,126,643

[45] Nov. 21, 1978

[54] BUTADIENE (1,3) CONVERSION

[75] Inventors: Timm E. Paxson; Milton M. Wald, both of Houston, Tex.

[73] Assignee: Shell Oil Company, Houston, Tex.

[21] Appl. No.: 850,875

[22] Filed: Nov. 14, 1977

[51] Int. Cl.$^2$ .......................... C07C 15/02; C10G 9/04
[52] U.S. Cl. ...................... 260/673; 252/441; 260/666 B; 260/668 R; 260/680 B
[58] Field of Search ............... 208/673, 676 R, 680 B, 208/666 B, 668 R

[56] References Cited

U.S. PATENT DOCUMENTS

| 2,492,984 | 1/1950 | Grosse et al. | 260/676 R |
|---|---|---|---|
| 2,979,543 | 4/1961 | Wilke et al. | 260/666 B |
| 3,458,585 | 7/1969 | Overmars et al. | 260/666 B |
| 3,660,342 | 5/1972 | Duggan | 260/666 A |
| 4,059,646 | 11/1977 | Wald et al. | 260/676 R |

OTHER PUBLICATIONS

Ansinger, "Mono-Olefins, Chemistry & Technology," 1968 Pergamon Press: p. 736, triptene, triptane.

A. Shaddan & P. W. Flanagan, "Alkylation with Alpha, Omega-dienes," ACS Pat. Div., Preprint 15-3, B60–B61.

Malinowski et al., Rocz. Chem. 48, pp. 359-360 (1974): "Dimerization & Oligomerization."

*Primary Examiner*—Delbert E. Gantz
*Assistant Examiner*—G. E. Schmitkons

[57] ABSTRACT

Method for the conversion of butadiene (1,3) comprising contacting butadiene (1,3) with zinc iodide, zinc bromide or mixtures thereof at a temperature of from about 150° C to about 550° C.

10 Claims, No Drawings

BUTADIENE (1,3) CONVERSION

BACKGROUND OF THE INVENTION

This invention relates to the conversion of butadiene (1,3) and more specifically, the cyclodimerization of butadiene (1,3). More particularly, the invention provides a novel process for the production of aromatic hydrocarbons, such as benzene, ethyl benzene, toluene, etc., utilizing a feedstock of butadiene (1,3).

SUMMARY OF THE INVENTION

Accordingly, the invention comprises a process in which butadiene (1,3) is contacted or reacted with a halide selected from zinc iodide, zinc bromide, or mixtures thereof, at a temperature of from about 150° C. to 550° C. Products of the reaction include a significant proportion of aromatic hydrocarbons, and the product stream may be used as a whole, if desired, or treated by conventional techniques to separate the aromatics, etc. In its preferred form, the invention comprises a process in which butadiene (1,3) is contacted with a material selected from zinc iodide, zinc bromide, or mixtures thereof, at a temperature of 170° C. to 500° C.

DETAILED DESCRIPTION OF THE INVENTION

The source of butadiene (1,3) is a matter of choice. The butadiene (1,3) need not be pure, provided the impurities or dilutants (or their reaction products) do not interfere significantly with the conversion. Thus, other diolefins, olefins, and alkanes, all of which are commonly present in refinery or petrochemical streams, may be present. It is an advantage of the invention that such streams may be employed and their butadiene (1,3) content upgraded to higher value products.

In the same manner, the zinc iodide or zinc bromide need not be pure, but may contain impurities which do not interfere with the reaction. Commercial grade zinc iodide and zinc bromide are acceptable in the process of the invention, and mixtures of the compounds may be used. Zinc chloride also promotes reaction of butadiene (1,3) at higher temperatures.

The temperatures employed in the reaction are significant. In general, the conversion of butadiene (1,3) is suitably carried out at temperatures of from about 150° C. to about 550° C., and preferably from about 150° C. or about 170° C. to about 500° C. At higher butadiene (1,3) ratios, and temperatures above about 250° C., cyclodimerization occurs in greater amounts, and significant proportions of aromatic compounds are produced. Accordingly, while cyclodimerization of the butadiene (1,3) occurs at temperatures below 250° C., the preferred temperatures for cyclodimerization are from about 250° C. to about 500° C.

Pressures employed in the reaction zone are not critical, and may vary widely. Thus, pressures may be atmospheric, below atmospheric, or greater than atmospheric. As a practical matter, pressure in a batch-type system may be atmospheric initially, but will rise as temperatures are raised. Pressures on the order of 2000 psig or even higher may be used, and the selection of the appropriate pressure to be employed is well within the skill of the art.

As indicated, the ratios of reactants are significant. The conversion of butadiene (1,3) requires that an effective amount of zinc iodide, zinc bromide, or their mixture, i.e., an amount sufficient to initiate and sustain the reaction, be employed. Those skilled in the art may readily determine appropriate amounts. For example, ratios of from about 0.01 mol of butadiene (1,3) per mol of $ZnI_2$ or $ZnBr_2$ to about 100 mols of butadiene (1,3) per mol of $ZnI_2$ may be used, while ratios of from about 0.1 mol of butadiene (1,3) per mol of $ZnI_2$ to about 20 mols of butadiene (1,3) per mol of $ZnI_2$ are preferred. In the case of mixtures of $ZnBr_2$ and $ZnI_2$, the ratios of mols of "mixture" to butadiene (1,3) are similar, the number of mols of "mixture" being the sum of the number of mols of each component.

The process may be conducted batch-wise or in a continuous fashion. Whichever procedure is employed, good mixing or contact of the butadiene, the $ZnI_2$, $ZnBr_2$, or their mixtures, is important for good results. Any reaction system which provides a high degree of mixing or contact of reactants may be employed. For example, fixed bed or slurry reactors may be used. Contact times are not critical, and those skilled in the art may vary the contact times to provide sufficient contact time to produce optimum results, depending on, e.g., volume of reactants, reactor design, temperatures, etc. For example, utilizing a slurry reactor design, and continuous flow of reactants, contact times on the order of from about 0.2 second to about 60 minutes, or ever longer, depending on the temperatures employed, may be used. In both batch and continuous procedures, it is not necessary that 100 percent conversion of the butadiene (1,3) be obtained before recovering the product. The product may be separated before use, or the reaction products mixture may be used as is for desired purposes.

DETAILED DESCRIPTION OF THE INVENTION

In order to describe the invention with greater particularity, reference is made to the following examples:

EXAMPLE I

A 300-ml, Hastelloy B autoclave was charged with 200 gms (626 mmol) of $ZnI_2$ and capped with 300 psig $N_2$. The reactor was sealed and pressure tested with $N_2$ gas. Butadiene (1,3) (10.0 gms, 185 mmol) was measured out and placed in a Jurguson vessel under the vapor pressure of butadiene (1,3). A pump was installed between the Jurguson and the autoclave, and the pumphead was cooled with Dry Ice to minimize vapor locking during butadiene (1,3) addition. The reactor was preheated to 200° C. and the butadiene (1,3) pumped in over a 10–15 minute time period. The reactor was maintained at 200° C. for an additional hour.

From the reactor was isolated 1.1 gms of an organic layer and a trace of an aqueous layer. Analysis of the organic products revealed the following composition.

| Compound | % weight |
| --- | --- |
| $C_4$–$C_6$ hydrocarbons | 5.5 |
| benzene | 0.4 |
| $C_7$ hydrocarbons | 3.4 |
| toluene | 1.0 |
| $C_8$ hydrocarbons | 18.9 |
| vinyl cyclohexane | 7.3 |
| ethyl benzene | 27.0 |
| xylenes | 3.0 |
| cyclooctadiene | 5.5 |
| $C_9$ hydrocarbons | 14.4 |
| $C_3$-benzenes | 1.4 |
| $C_4$-benzenes | 1.2 |
| indanes | 0.3 |
| $C_{10}$ hydrocarbons | 1.7 |
| $C_{11}$ hydrocarbons | 1.2 |

| Compound | % weight |
|---|---|
| C$_{12}$ hydrocarbons | 3.6 |
| C$_{12}$+ hydrocarbons | 4.0 |
| | 99.8 |

EXAMPLE II

A 300-ml, Hastelloy B autoclave was charged with 200 gms (626 mmol) of ZnI$_2$. The reactor was sealed and pressure tested with N$_2$ gas. Butadiene (1,3) 20.1 gm (370 mmol) was measured out and placed in Jurguson vessel under a pressure of 300 psig. The Jurguson and pump head were cooled with Dry Ice to minimize vapor locking during butadiene addition. The reactor was heated to 450° C. and the butadiene added over a 30-minute period. The reactor was maintained at 450° C. an additional 10 minutes. The reaction yielded 3.7 gms of an organic layer and a trace of an aqueous layer.

| Compound | Weight % |
|---|---|
| C$_4$ hydrocarbons | 4.6 |
| 1,3-C$_4$H$_6$ | 7.2 |
| C$_5$-C$_6$ hydrocarbons | 3.4 |
| C$_6$H$_6$ (benzene) | 7.0 |
| CH$_3$C$_6$H$_5$ (toluene) | 18.4 |
| C$_2$H$_5$C$_6$H$_5$ (ethyl benzene) | 7.1 |
| (CH$_3$)$_2$C$_6$H$_4$ (xylenes) | 14.3 |
| Higher boiling, volatile products | 23.0 |
| | 85.0 |

What is claimed is:

1. Process for the conversion of butadiene (1,3) comprising, contacting butadiene (1,3) and a material selected from zinc iodide, zinc bromide, and mixtures thereof at a temperature of from about 150° C. to about 550° C.

2. The process of claim 1 wherein the temperature is from about 150° C. to about 500° C.

3. The process of claim 1 wherein the temperature is from about 170° C. to about 500° C.

4. The process of claim 1 wherein the temperature is from about 250° C. to about 550° C.

5. The process of claim 1 wherein the temperature is from about 250° C. to about 500° C.

6. The process of claim 2 wherein the material is zinc iodide.

7. The process of claim 3 wherein the material is zinc bromide.

8. The process of claim 3 wherein the material is a mixture of zinc iodide and zinc bromide.

9. The process of claim 4 wherein the material is zinc iodide.

10. The process of claim 5 wherein the material is zinc iodide.

* * * * *